(12) United States Patent
Li et al.

(10) Patent No.: US 10,895,521 B2
(45) Date of Patent: Jan. 19, 2021

(54) FULL-VIEW-FIELD QUANTITATIVE STATISTICAL DISTRIBUTION CHARACTERIZATION METHOD OF PRECIPITATE PARTICLES IN METAL MATERIAL

(71) Applicant: Central Iron and Steel Research Institute, Beijing (CN)

(72) Inventors: Dongling Li, Beijing (CN); Xuejing Shen, Beijing (CN); Lei Zhao, Beijing (CN); Haizhou Wang, Beijing (CN); Weihao Wan, Beijing (CN); Bing Han, Beijing (CN); Yuhua Lu, Beijing (CN); Feifei Feng, Beijing (CN); Chao Li, Beijing (CN)

(73) Assignee: CENTRAL IRON AND STEEL RESEARCH INSTITUTE, Beijing (CN)

( * ) Notice: Subject to any disclaimer, the term of this patent is extended or adjusted under 35 U.S.C. 154(b) by 208 days.

(21) Appl. No.: 16/232,282

(22) Filed: Dec. 26, 2018

(65) Prior Publication Data

US 2019/0204199 A1    Jul. 4, 2019

(30) Foreign Application Priority Data

Dec. 29, 2017   (CN) .......................... 2017 1 1469419

(51) Int. Cl.
*G01N 15/02*    (2006.01)
*G01N 1/32*     (2006.01)
(Continued)

(52) U.S. Cl.
CPC ........... *G01N 15/0227* (2013.01); *G01N 1/32* (2013.01); *G01N 15/1475* (2013.01);
(Continued)

(58) Field of Classification Search
CPC .................................................. G01N 15/0227
See application file for complete search history.

(56) References Cited

U.S. PATENT DOCUMENTS

2014/0344013 A1* 11/2014 Karty ................. G06Q 30/0201
705/7.29

FOREIGN PATENT DOCUMENTS

CN       102494976 A      6/2012
CN       102879412 A  *   1/2013
(Continued)

*Primary Examiner* — Manuel A Rivera Vargas
(74) *Attorney, Agent, or Firm* — Muncy, Geissler, Olds & Lowe, P.C.

(57) ABSTRACT

The invention belongs to the technical field of the quantitative statistical distribution analysis of the features from characteristic images of microstructures and precipitated phases in metal materials, and relates to a quantitative statistical distribution characterization method of precipitate particles with the full field of view in a metal material. The method comprises the following steps of electrolytic corrosion of a metallic material specimen, automatic collection of characteristic images of microstructure, automatic stitching and fusion of the full-view-field microstructure images, automatic identification and segmentation of the precipitate particles and quantitative distribution characterization of the precipitate particles with the full field of view in a large-range scale. By establishing a mathematic model, the large-range automatic stitching and fusion of the characteristic images of the full-view-field microstructures in a characteristic region and the automatic segmentation and identification of the precipitate particles are realized; and the quantitative statistical distribution characterization information of the full-view-field morphology, quantity, size, distribution and the like of plentiful precipitated phases in a larger range is quickly obtained. The method has the features of being accurate, high-efficiency and informative in quantitative (Continued)

distribution characterization, as well as has much more statistical representativeness compared with conventional single-view-field quantitative image analysis.

7 Claims, 5 Drawing Sheets

(51) Int. Cl.
| | |
|---|---|
| *G06T 3/00* | (2006.01) |
| *G06K 9/00* | (2006.01) |
| *G06T 7/174* | (2017.01) |
| *G01N 15/14* | (2006.01) |
| *G01N 33/20* | (2019.01) |
| *G06T 7/70* | (2017.01) |
| *C25F 3/22* | (2006.01) |
| *G01N 15/00* | (2006.01) |

(52) U.S. Cl.
CPC ........... *G01N 33/20* (2013.01); *G06K 9/0014* (2013.01); *G06T 3/0068* (2013.01); *G06T 7/174* (2017.01); *C25F 3/22* (2013.01); *G01N 2015/0061* (2013.01); *G06T 7/70* (2017.01); *G06T 2207/10056* (2013.01); *G06T 2207/10148* (2013.01); *G06T 2207/20152* (2013.01); *G06T 2207/20221* (2013.01); *G06T 2207/30136* (2013.01)

(56) References Cited

FOREIGN PATENT DOCUMENTS

| | | |
|---|---|---|
| CN | 103196733 A | 7/2013 |
| CN | 104764647 A | 7/2015 |
| CN | 103207179 B | 4/2016 |
| CN | 107314928 A | 11/2017 |

* cited by examiner

FULL-VIEW-FIELD QUANTITATIVE STATISTICAL DISTRIBUTION CHARACTERIZATION METHOD OF PRECIPITATE PARTICLES IN METAL MATERIAL

TECHNICAL FIELD

The invention belongs to the technical field of the quantitative statistical distribution analysis the features from characteristic images of microstructures and precipitated phases in metal materials, and relates to a full-view-field quantitative statistical distribution characterization method of precipitate particles in a metal material.

BACKGROUND

Phases distributed in a matrix with a discontinuous state and impossibly including other phases therein in material are collectively called precipitated phases. Precipitated phase is a new phase precipitated in grain interior and grain boundary and having crystal structure or lattice constant different from a matrix structure, and there is a clear interface between the precipitated phase and the matrix structure. Therefore, the precipitated phase plays an important role in steel, and has important influence on the strength, toughness, plasticity, deep-drawing property, fatigue, attrition, fracture, corrosion and important mechanical and chemical properties of steel. For example, two basic constituent phases of the precipitation hardening type nickel-based superalloy are γ phase and γ' phase, the γ' phase is the most important precipitated phase thereof, wherein the γ' phases in the polycrystal nickel-based superalloy exist in grain interior and grain boundary in the form of near-spherical particles, and the volume fraction, distribution, size and morphology of γ' phase particles are key factors affecting alloy mechanical properties, especially high-temperature properties. Similarly, in some ultra supercritical heat-resistant steel, for the precipitated phases, i.e. Laves phases of the intermetallic compound generated in the aging process, the number, size and distribution of the particles thereof may have great influence on the high-temperature strength and corrosion resistance of the heat-resistant steel. Therefore, the statistical quantitative distribution analysis of some precipitate particles in the metal material has important significance for the study of the metal material.

At present, the morphology and particle size of precipitate particles are mainly observed through metallographic and electron microscope methods, and by analyzing the characteristic image thereof, the particle size thereof is obtained and the volume fraction is calculated. However, the above methods are all used to perform particle statistics in single view field, meanwhile, morphology processing and particle separation are performed using a manual method, and then particle counting and statistics are performed using image software, so that not only the statistical efficiency is low, but also because the non-homogeneity of material decides that such measurement mode lacks of statistical representativeness, it is difficult to guarantee the accuracy, and is unable to meet the requirements of quantitative statistical distribution characterization of precipitated phases in metal within a larger range.

At present, there are three problems that obstruct the quick quantitative statistical distribution analysis of precipitate particles in metallurgical characteristic images: first, if general polishing and chemical corrosion are performed on precipitated phases and a matrix structure, the precipitated phases falls off or is not clear distinguished from the matrix structure; similarly, it is difficult to quantitatively retain precipitate particles if not selecting an appropriate electrolytic corrosion condition, so that quantitative metallurgical statistical software cannot make accurate statistics. Second, the observed view fields are limited, microstructure images are collected through several single view fields, and the observed range and counted particles are limited, being unable to represent the distribution state of precipitated phases of the material within a large range. Third, there is a lack of algorithms for processing metallurgical image data, and the segmentation of microstructures is realized only through binaryzation, causing incorrect judgment of many adhered particles.

SUMMARY

Aiming at the above technical problems, the purpose of the present invention is to provide a full-view-field quantitative statistical distribution characterization method of precipitate particles in a metal material, to eliminate subjective errors caused by manually selecting view fields and avoid statistical omission of precipitate particles, solve the problem of low efficiency caused by manually modifying images, and provide a more representative, comprehensive, accurate and high-efficient detection means for large-range full-view-field quantitative statistical distribution characterization of precipitate particles in a metal material while taking account of the feature of inhomogeneity of the material.

To achieve the above purpose, the present invention provides the following technical solution:

the present invention provides a full-view-field quantitative statistical distribution characterization method of precipitate particles in a metal material, the method comprising the following steps:

(1) Electrolytic Polishing and Corrosion of a Metallic Material Specimen:

first, performing electrolytic polishing on the metallic material specimen after mechanical polishing is performed, so that the surface of the metallic material specimen is bright, clean and smooth; and then, performing electrolytic corrosion on the metallic material specimen after electrolytic polishing is performed, so that precipitate particles stand out of the surface of the metallic material specimen;

(2) Automatic Collection of Characteristic Images of Microstructures:

positioning and marking a characteristic region of the surface of the metallic material specimen after electrolytic corrosion is performed, performing automatic collection of characteristic images of full-view-field microstructures on the marked region using a full-automatic metallographic microscope, to obtain a plurality of characteristic images of full-view-field microstructures containing precipitate particles combined with image synthesis; and meanwhile, recording three-dimensional coordinates of the precipitate particles in different focusing positions, to obtain a plurality of 3D morphology distribution diagrams of the precipitate particles;

(3) Automatic Stitching and Fusion of the Characteristic Images of Full-View-Field Microstructures;

for the plurality of clear characteristic images of full-view-field microstructures containing precipitate particles obtained in the step (2), acquiring mutual information for searching the characteristic images of metallurgical structures through the entropies and joint entropy of any two characteristic images of metallurgical structures of different view fields using a mutual information-based image registration algorithm, and determining the position and size of adjacent overlap regions, so that the automatic identification and stitching of the overlap regions of the characteristic images of full-view-field microstructures are realized; and performing mathematical processing on edge grayscales of the spliced characteristic images of the full-view-field metallurgical structures, so that the grayscales are homogenized and fused, and a characteristic image of large-range full-view-field metallurgical structure containing a plurality of precipitate particles is obtained finally;

(4) Automatic Identification and Segmentation of Precipitate Particles:

performing noise elimination, segmentation, binarization, hole filling, fragment removal and other preprocessing on the characteristic image of the large-range full-view-field microstructure containing a plurality of precipitate particles obtained in the step (3), to obtain a preprocessed image; performing Euclidean distance transformation on the preprocessed image; and performing segmentation on the preprocessed image on which Euclidean distance transformation is performed with a watershed algorithm, to obtain a segmented characteristic image of the full-view-field microstructure; and (5) Quantitative Distribution Characterization of Large-Range Full-View-Field Precipitate Particles:

performing statistical distribution analysis of precipitate particles on the 3D morphology distribution diagrams of the precipitate particles obtained in the step (2) and on the segmented characteristic image of the full-view-field microstructure obtained in the step (4), to obtain the position, morphology, area and equivalent circle diameter of each precipitate particle in the large-range full view field and quantitative statistical distribution data of particle number distribution and area fraction distribution within different particle size ranges.

In the step (1), the metallic material specimen on which mechanical polishing is performed is taken as an anode, and a stainless steel sheet is taken as a cathode;

in the process of electrolytic polishing, the electrolytic solution is a mixed solution of inorganic acid and methanol, wherein the volume ratio of inorganic acid to methanol is 1:3 to 1:4, the voltage is 20V-40V, and the electrolytic duration is 10 s-100 s; and in the process of electrolytic corrosion, the electrolytic solution is a mixed solution of inorganic acid and chromic trioxide, wherein the voltage is 0.1V-5V, the electrolytic duration is 1 s-30 s, and the electrolytic temperature is 0° C.-25° C., wherein the mixed solution of inorganic acid and chromic trioxide is prepared by adding 10 g-20 g of chromic trioxide into 150 mL-200 mL of inorganic acid solution.

The inorganic acid in the process of electrolytic polishing is sulfuric acid; the inorganic acid in the process of electrolytic corrosion is a mixed solution of sulfuric acid and phosphoric acid, and the volume ratio of sulfuric acid to phosphoric acid is 1:15 to 1:20.

In the step (1), the surface of the metallic material specimen on which electrolytic corrosion is performed is immersed and washed by citric acid-aqueous solution and deionized water in sequence, and finally, the surface of the metallic material specimen is washed by absolute ethyl alcohol and is naturally dried, to guarantee the precipitate particles of the surface of the metallic material specimen against loss.

In the step (2), characteristic images of microstructures of all view fields are processed using extension of depth of field: overlapping a plurality of characteristic images of microstructures in different focusing positions of the same view field in the marked region, to generate a clear characteristic image of microstructure containing precipitate particles finally.

In the step (3), the process of the mutual information-based image registration algorithm is as follows:

the expression of the entropy is as follows:

$$H(X) = -\sum_{j=1}^{N} p_j \log P_j$$

where $P_j$ represents the probability distribution of the $j^{th}$ variable;

the joint entropy reflects the correlation between the random variables X and Y, and the expression thereof is as follows:

$$H(X, Y) = -\sum_{x,y} P_{XY}(x, y) \log P_{XY}(x, y)$$

where $P_{XY}(x, y)$ represents the joint probability distribution of x and y; for any two characteristic images A and B of microstructures of different view fields, the mutual information thereof is expressed as:

$$MI(A,B) = H(A) + H(F) - H(A,B)$$

where H (A) represents the entropy of A, H (B) represents the entropy of B, and H (A, B) represents the joint entropy of A and B.

In the step (4), the formula of Euclidean distance transformation is as follows:

$$\mathrm{disf}(p(x_1,y_1),q(x_2,y_2)) = \sqrt{(x_1-x_2)^2+(y_1-y_2)^2},$$

where p and q represent two points in the image, (x1, y1) and (x2, y2) respectively represent coordinates of p and q, and disf (p, q) represents the Euclidean distance between two points, i.e. the segment length between two points.

The method is used to analyze precipitates in a precipitation hardening type nickel-based superalloy.

Compared with the prior art, the present invention has the advantageous effects that:

1. For the existing metallographic analysis, microstructure may be observed using a chemical corrosion method in general, causing that some precipitate particles fall off and a precipitated phase is not clearly distinguished from a matrix structure. In high alloy steels, electrolytic corrosion may be used sometimes, but if electrolytic conditions are not appropriately selected, although the morphology of some precipitate particles may be seen, it is unable to guarantee the quantitative retention of precipitate particles.

In the present invention, the precipitated phase is interface-separated from the matrix structure using specific electrolytic polishing and electrolytic corrosion methods, so that precipitate particles quantitatively stand out of the material surface, and microstructure images containing precipitate particles are completely and clearly collected by means of extension of depth of field.

2. The existing metallographic image method is mainly used to perform image analysis on single view field, and the observed view field areas and structures are limited. Although the scanning electron microscope may observe the morphology and distribution of some small precipitated phases, similarly, the observed view fields are limited, so that it is unable to realize automatic collection of a plurality of view fields.

By means of the present invention, through automatic collection, fusion and stitching of large-range full view field images, characteristic images of full-view-field microstructures and precipitated phases within a larger characteristic region may be obtained.

3. The existing quantitative metallurgical analysis software may perform statistics on the particles in single microstructure images. However, because particles are distinguished only through binarization, for some adhered particles and incomplete particles located at image edge, incorrect detection or missing detection may occur, thus causing poor reliability of statistical data. If the current metallographic image analysis method is used to separate particles, the method of manually modifying images must be used, so that the analysis efficiency is low, and the subjectivity is strong.

In the present invention, by performing mathematics processing on the data of metallographic characteristic images, analysis of adhered particles is realized. Meanwhile, because statistical analysis of particles is performed on stitching full-view-field images, the phenomenon of incomplete statistics of a plurality of particles at the edge during observation of single view fields is greatly eliminated. Therefore, the present invention has the advantages of large statistical view field and high efficiency, and the statistical data are more accurate and reliable.

Figure 1:
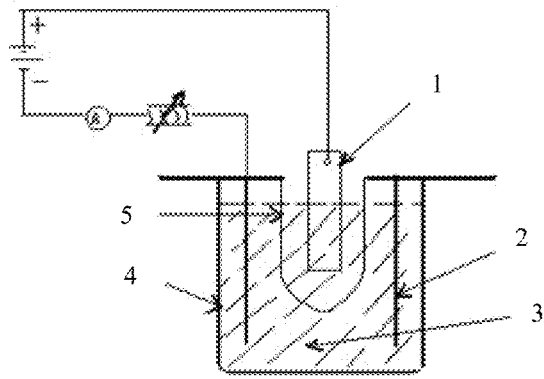
FIG. 1 is a structural schematic diagram of an electrolytic test device used in the present invention.

In the drawings, reference numerals are:
1. Metallic material specimen
2. Stainless steel cathode
3. Beaker
4. Electrolytic solution
5. Rubber capsule
6. Local minimum
7. Basin
8. Watershed
9. Dam

DETAILED DESCRIPTION

The present invention provides a full-view-field quantitative statistical distribution characterization method of precipitate particles in a metal material, comprising: electrolytic corrosion of a metallic material specimen, automatic collection of characteristic images of microstructures, automatic stitching and fusion of the characteristic images of full-view-field microstructures, automatic identification and segmentation of the precipitate particles and quantitative distribution characterization of the large-range full-view-field precipitate particles. The specific steps are as follows:

(1) Electrolytic Polishing and Corrosion of a Metallic Material Specimen:

electrolytic corrosion is performed on the metallic material specimen using an electrolytic test device shown in FIG. 1, the electrolytic test device comprising a beaker 3 containing an electrolytic solution 4, a rubber capsule 5 (rubber object playing a role of a diaphragm) dividing the beaker 3 into of an anode chamber and a cathode chamber, and a power source which may control the voltage and is respectively connected with a stainless steel cathode 2 located in the cathode chamber and a metallic material specimen 1 located in the cathode chamber;

the metallic material specimen after mechanical polishing is performed as an anode and a stainless steel sheet as a cathode, electrolytic polishing is performed on the metallic material specimen at room temperature and certain voltage by taking a mixed solution of inorganic acid and methanol as an electrolytic solution according to the type of metal material, the duration of electrolytic polishing is controlled, and the influence of surface scratches and other adhered particles is eliminated, so that the surface of the metallic material specimen is bright and clean and smooth;

then, electrolytic corrosion is performed in the mixed solution of inorganic acid and chromic oxide, selective corrosion is made to occur on the surface of the metallic material specimen through appropriate voltage, electrolytic temperature and electrolytic duration using the decomposition potential difference between the matrix and the precipitated phase, and the matrix is preferentially electrolyzed, so that the precipitate particles appear on the material surface; meanwhile, the electrolytic surface of the metallic material specimen is immersed and washed by citric acid-aqueous solution or other solution and deionized water in sequence, and finally, the surface of the metallic material specimen is washed by absolute ethyl alcohol and is naturally dried, to guarantee the precipitate particles of the surface of the metallic material specimen against loss, wherein in the process of electrolytic polishing, the voltage is 20V-40V, and the electrolytic duration is 10 s-100 s; and in the process of electrolytic corrosion, the voltage is 0.1V-5V, the electrolytic duration is 1 s-30 s, and the electrolytic temperature is 0□-25□.

(2) Automatic Collection of Characteristic Images of Metallurgical Structures:

a characteristic region of the surface of the metallic material specimen after electrolytic corrosion is marked, automatic collection of characteristic images of full-view-field microstructures is performed on the marked region using a full-automatic metallographic microscope, to automatically collect more than $10^4$ piece of characteristic images according to the size of the marked region. Because the precipitate particles stand out of the surface of matrix, and the diameter of each precipitate particle is 1-10 microns, the altitudes of the precipitate phase and matrix on the surface of the metal material may be different. Thus, the depths of field during focusing are inconsistent, and must perform extension of depth of field. A plurality of characteristic images of microstructures in different focusing positions of the same view field in the marked regions are overlapped, to obtain a plurality of clear characteristic images of full-view-field microstructures containing precipitate particles combined with image synthesis. Meanwhile, three-dimensional coordinates of the precipitate particles in different focusing positions are recorded, to obtain a plurality of 3D morphology distribution diagrams of the precipitate phase particles;

(3) Automatic Stitching and Fusion of the Characteristic Images of Full-View-Field Metallurgical Structures:

for the clear characteristic images of full-view-field metallurgical structures containing precipitate particles generated through automatic collection and extension of depth of field, mutual information of the characteristic images of metallurgical structures is acquired through the entropies and joint entropy of any two characteristic images of microstructures of different view fields using a mutual information-based image registration algorithm, and the position and size of adjacent overlap regions are determined, so that the identification and stitching of the overlap regions of the characteristic images of full-view-field metallurgical structures are realized; meanwhile, mathematics processing is performed on edge grayscales of the spliced characteristic images of full-view-field microstructures, so the grayscales are homogenized and fused, and a characteristic image of large-range full-view-field metallurgical structure containing a plurality of precipitate particles is obtained finally.

(4) Automatic Identification and Segmentation of Precipitate Particles:

a watershed algorithm used in mathematics is introduced to realize automatic identification and segmentation of precipitate particles, specifically including:

a) performing noise elimination, segmentation, binarization, hole filling, fragment removal and other preprocessing on the obtained characteristic image of the large-range full-view-field metallurgical structure containing a plurality of precipitate particles, to obtain a preprocessed image;

b) performing Euclidean distance transformation on the preprocessed image, to realize objective refinement, skeleton extraction, shape interpolation & match and separation of adhered objects; and c) performing segmentation on the preprocessed image on which Euclidean distance transformation is performed with a watershed algorithm, to obtain a segmented characteristic image of the full-view-field microstructures.

Figure 2:
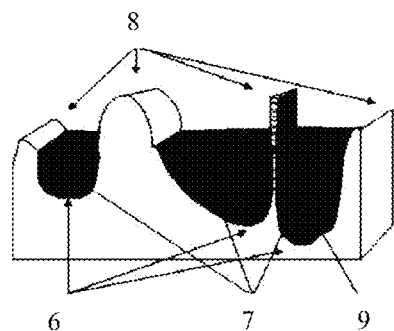
FIG. 2 is a schematic diagram of a watershed algorithm of the present invention.

The grayscale value of the pixel of each point in the preprocessed image on which Euclidean distance transformation is performed represents the altitude of the point, and each local minimum 6 and affected region thereof are called basins 7, the boundaries of the basins 7 form a watershed 8, and the edges of different basins 7 construct a dam 9 (as shown in FIG. 2).

(5) Quantitative Distribution Characterization of Large-Range Full-View-Field Precipitate Particles:

statistical distribution analysis of precipitate particles is performed on the 3D morphology distribution diagrams of the precipitate particles and on the segmented characteristic image of the full-view-field metallurgical structure, to obtain the position, morphology, area and equivalent circle diameter of each precipitate particle of the large-range full view field and quantitative statistical distribution data of particle number distribution and area fraction distribution within different particle size ranges.

The present invention is further described below in combination with drawings and embodiments.

Embodiments

This embodiment describes a nickel-based superalloy for an aero-engine turbine disk. The precipitation hardening type nickel-based superalloy is a key heat-resistant material for manufacturing aero-engines, gas turbines, nuclear reaction devices and the like, and the development level thereof becomes an important mark indicating the aviation industry level of a country. With the improvement of engine thrust-to-weight ratio and performance requirements, the turbine inlet temperature is constantly increased, and then higher requirements for turbine disk alloy bearing temperature are proposed. Because of the specificity of the size of the aero-engine turbine disk, difference exists in processes and heat treating regimes of various parts, especially the cooling rate may form graded distribution on the thickness section, causing that difference exists in the number, size and distribution of γ' phases in different regions. Therefore, a reliable influence rule of γ' phases on high temperature properties may be obtained only when quantitative statistical distribution characterization is performed on the γ' phases of the nickel-based superalloy within a larger range, thereby guiding process improvement and property improvement.

By taking two superalloys for aero-engine turbine disks having different high temperature creep properties as examples, a full-view-field quantitative statistical distribution characterization method of γ'-phase particles in a precipitation hardening type nickel-based superalloy is proposed.

□. Electrolytic Polishing and Corrosion of Material (1) Electrolytic Polishing of Material:

a first specimen and a second specimen cut from different parts of a turbine disk are prepared into a bright and clean mirror surface through coarse grinding, fine grinding, polishing and other step, room-temperature electrolytic polishing is performed again using the device shown FIG. 1 in a mixed solution of sulfuric acid and methanol of 1:3 to 1:4 (V/V), wherein the voltage is 20V-40V, and the electrolytic duration is 10 s-100 s, scratches or other particles remaining on the surface are further eliminated, so that the surface to be detected is smoother.

(2) Electrolytic Corrosion of Material:

electrolytic corrosion is performed on the first specimen and second specimen after electrolytic polished in a certain proportion of mixed solution of phosphoric acid, sulfuric acid and chromic trioxide, wherein the electrolytic voltage is 0.1V-5V, the electrolytic duration is 1 s-30 s, and the electrolytic temperature is 0□-25□, through the decomposition potential difference between the matrix and γ' phase, the matrix is selectively dissolved, so that the γ'-phase particles raised appear on the material surface, the electrolytic surface of the specimen is immersed and washed by 1% (m/V) citric acid-aqueous solution and deionized water in sequence, and finally, the surface of the specimen is washed by absolute ethyl alcohol absolute ethyl alcohol and is naturally dried, wherein the mixed solution of phosphoric acid, sulfuric acid and chromic trioxide is prepared by adding 10 g-20 g of chromic trioxide into 150 mL-200 mL of mixed solution of sulfuric acid and phosphoric acid (volume ratio being 1:15 to 1:20).

II. Automatic Collection of Characteristic Images of Microstructures

The characteristic regions of the surfaces of the first specimen and the second specimen after electrolytic corrosion are positioned and marked by indentation using a Vickers hardness tester, when amplified to 1000 times, the number of the automatically collected view fields designed is 10×10, i.e. the number of view fields in the X direction is 10, the number of view fields in the Y direction is 10, and characteristic images of microstructures of γ' phases of 100 view fields are obtained finally.

Figure 3:
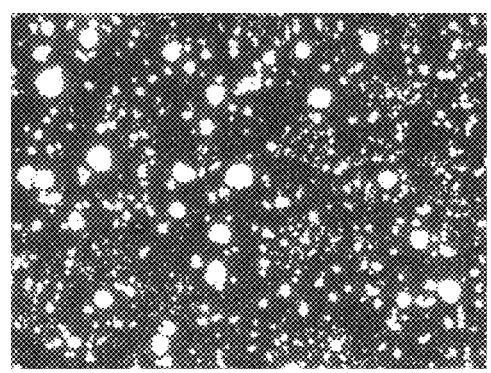
FIG. 3 shows a characteristic image of a microstructure after extension of depth of field of embodiments of the present invention.

Collection of characteristic images of full-view-field metallurgical structures is performed on the marked characteristic regions using a full-automatic metallographic microscope, because the γ'-phase particles stand out of the material surface, there may be a different altitude between the precipitated phase and the matrix in altitude, and the altitude difference may reach several microns, so that the depths of field during focusing may be inconsistent, and only through extension of depth of field, a plurality of characteristic images of microstructures in different focusing positions of the same view field in the marked regions are overlapped, to generate a clear characteristic image of metallurgical structure of γ' phases (as shown in FIG. 3), thus a clear characteristic image of full-view-field metallurgical structure containing precipitate particles is obtained finally.

Figure 4:
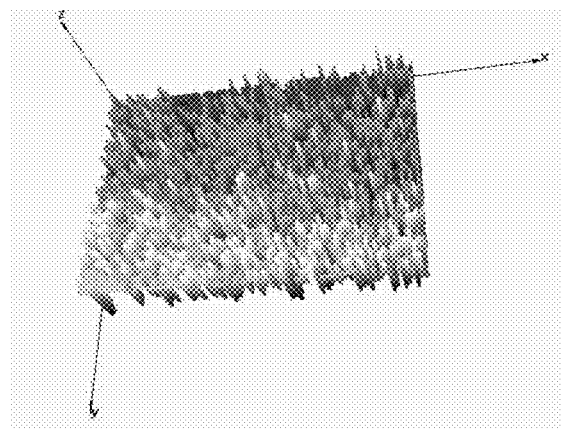
FIG. 4 is a 3D morphology distribution diagram of γ'-phase particles of embodiments of the present invention.

Meanwhile, three-dimensional coordinates of the γ' phases in different focusing positions are recorded, to obtain 3D morphology distribution diagrams of the γ' phases (as shown in FIG. 4).

III. Automatic Stitching and Fusion of the Characteristic Images of Full-View-Field Microstructures For the clear characteristic images of full-view-field metallurgical structures containing precipitate particles generated through automatic collection and extension of depth of field, the entropies and joint entropy of any two characteristic images (A and B) of metallurgical structures of different view fields are calculated.

Figure 5:
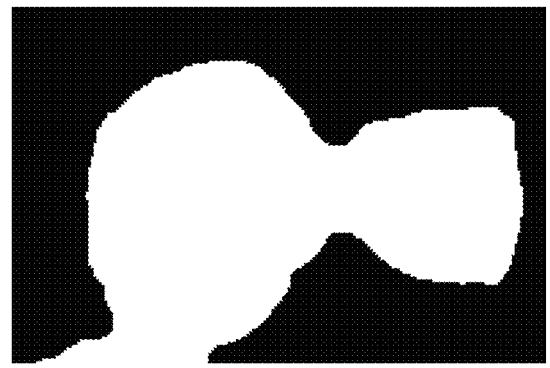
FIG. 5 shows an image after noise elimination, segmentation, binarization, hole filling, fragment removal and other preprocessing of embodiments of the present invention.

The expression of the entropy is as follows:

$$H(X) = -\sum_{j=1}^{N} p_j \log P_j$$

where $P_j$ represents the probability distribution of the $j^{th}$ variable;

the joint entropy reflects the correlation between the random variables X and Y, and the expression thereof is as follows:

$$H(X, Y) = -\sum_{x,y} P_{XY}(x, y) \log P_{XY}(x, y)$$

where $P_{XY}(x, y)$ represents the joint probability distribution of x and y; for any two characteristic images A and B of microstructures of different view fields, the mutual information thereof is expressed as:

$$MI(A,B) = H(A) + H(F) - H(A,B)$$

where H (A), H (B) and H (A, B) respectively represent the entropies of A and B and the joint entropy thereof. The higher the similarity between two images or the larger the overlap part is, the larger the mutual information is. By calculating the mutual information of the images, an image region matching with the edge of each image is found, the position and size of adjacent images and overlap regions are determined, and then automatic stitching is performed. Meanwhile, the edge grayscales of the spliced characteristic images of full-view-field metallurgical structures are homogenized and fused, and a characteristic image (FIG. 5) of large-range full-view-field metallurgical structure containing a plurality of γ'-phase particles is obtained finally.

IV. Automatic Identification and Segmentation of γ'-Phase Particles

A watershed segmentation method used in mathematics is introduced to realize automatic identification and segmentation of γ'-phase particles, and the specific algorithm is realized through the MATLAB software editing program. The grayscale value of the pixel of each point in the image represents the altitude of the point, and each local minimum and affected region thereof are called 'basins', and the boundaries of the basins form a watershed. Meanwhile, distance transformation is performed on the binary image, so as to achieve object refinement, skeleton extraction, shape interpolation and separation of matched and adhered objects and so on. For determining the distance, the Euclidean distance formula used in the present invention is as follows:

$$\text{disf}(p(x_1,y_1),q(x_2,y_2)) = \sqrt{(x_1-x_2)^2 + (y_1-y_2)^2},$$

where p and q represent two points in the image, (x1, y1) and (x2, y2) respectively represent coordinates of p and q, and disf (p, q) represents the Euclidean distance between two points, i.e. the segment length between two points.

Figure 6:
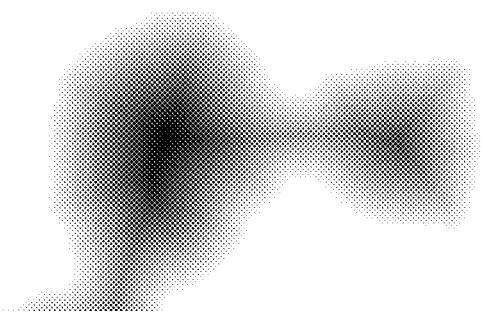
FIG. 6 shows an image obtained after Euclidean distance transformation of embodiments of the present invention.
Figure 7:
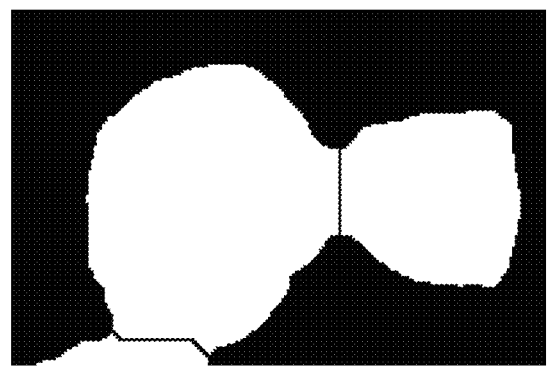
FIG. 7 shows a watershed line formed after automatic segmentation of embodiments of the present invention.

The process of separating adhered particles using the watershed segmentation method combined with distance transformation is as follows:

a) first, performing noise elimination, segmentation, binarization, hole filling, fragment removal and other preprocessing on the obtained characteristic image (FIG. 5) of the large-range full-view-field microstructure containing a plurality of precipitate particles, to obtain a preprocessed image (FIG. 6);

b) performing Euclidean distance transformation on the preprocessed image, to obtain FIG. 7; and c) performing a segmentation in a watershed on the preprocessed image on which Euclidean distance transformation is performed using a watershed algorithm, to obtain a segmented characteristic image of the full-view-field microstructure.

Figure 8:
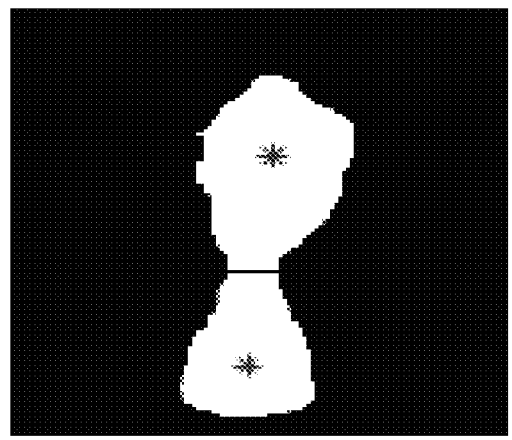
FIG. 8 is an effect diagram of automatic segmentation of particles in a local region of a first specimen of embodiments of the present invention.
Figure 9:
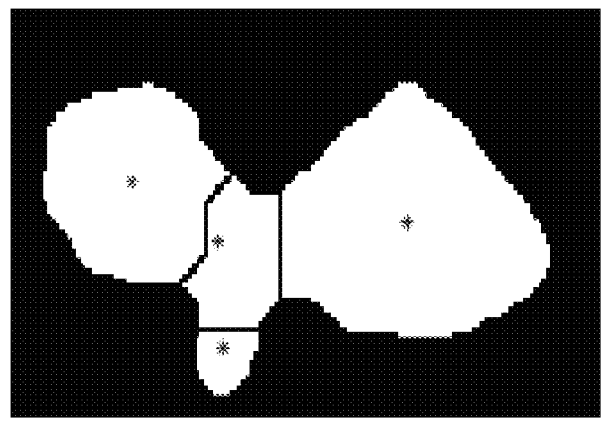
FIG. 9 is an effect diagram of automatic segmentation of particles in a local region of a second specimen of embodiments of the present invention.

By means of this method, it is found that the adhered particles are well segmented. The effect of automatic segmentation of particles of a local region of the first specimen is as shown in FIG. 8, and the effect of automatic segmentation of particles of a local region of the second specimen is as shown in FIG. 9.

V. Quantitative Statistical Distribution Characterization of γ' Phase Particles within Full-View-Field Range Through particle statistical distribution analysis performed on the 3D morphology distribution diagrams of the γ' phases and the characteristic images of the full-view-field microstructures containing particles segmented, quantitative data (Table 1) such as the area and equivalent circle diameter of each γ'-phase particle of the whole large-range full view field may be obtained, and meanwhile, through statistical calculation, data (Table 2, Table 3) such as particle number distribution and area fraction distribution within different particle size ranges of γ'-phase particles within the full-view-field range may be quickly obtained.

Meanwhile, as a comparative example, binarization, noise elimination and particle segmentation are performed on 100 metallographic pictures collected from the two specimens using a method of manually modifying images, and the data thereof are as shown in Table 4 and Table 5.

Figure 10:
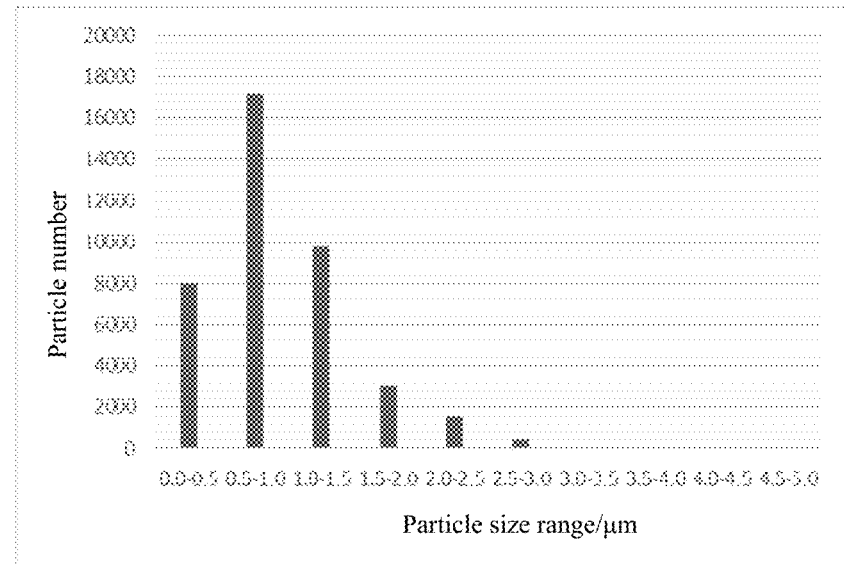
FIG. 10 is a statistical distribution diagram of particles of a first specimen of embodiments of the present invention.
Figure 11:
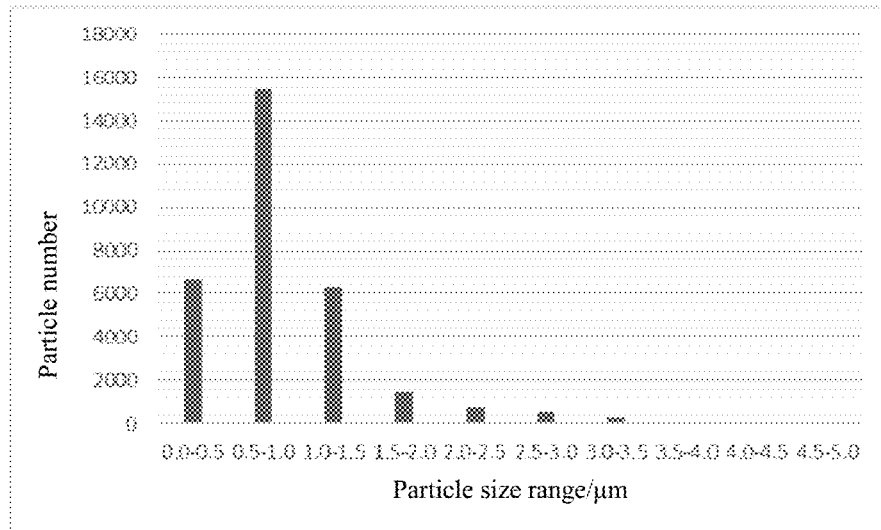
FIG. 11 is a statistical distribution diagram of particles of a second specimen of embodiments of the present invention.

It is found by comparison that the present invention has good consistency in the result of automatic stitching, segmentation and statistics of full-view-field precipitate particles of characteristic regions of a superalloy and the quantitative metallographic result obtained through the complicated process of manually modifying images, but greatly increases the analysis efficiency. The statistical distribution of particles of the first specimen is as shown in FIG. 10, and the statistical distribution of particles of the second specimen is as shown in FIG. 11. It is found that there is a great difference between distributions of $\gamma'$-phase particles in the superalloys of the first specimen and the second specimen, thus causing a difference between high temperature creep properties of the first specimen and the second specimen.

TABLE 1

Statistical Data of Particle Size Distribution

| | Equal-area-circle diameter distribution | | | | | | | | | |
|---|---|---|---|---|---|---|---|---|---|---|
| | 1.009 | 2.008 | 3.007 | 4.006 | 5.005 | 6.004 | 7.003 | 8.002 | 9.001 | 10 |
| Particle number | 61 | 86 | 57 | 28 | 20 | 11 | 3 | 1 | 0 | 0 |
| Number percentage | 22.85% | 32.21% | 21.35% | 10.49% | 7.49% | 4.12% | 1.12% | 0.37% | 0.00% | 0.00% |
| Equal-area-circle diameter percentage | 5.48% | 22.72% | 24.61% | 16.48% | 15.46% | 10.61% | 3.39% | 1.24% | 0.00% | 0.00% |
| Classification area content | 0.14% | 1.39% | 2.42% | 2.19% | 2.70% | 2.31% | 0.86% | 0.34% | 0.00% | 0.00% |
| Accumulated number percentage | 22.85% | 55.06% | 76.40% | 86.89% | 94.38% | 98.50% | 99.63% | 100.00% | 100.00% | 100.00% |
| Accumulated equivalent circle diameter percentage | 5.48% | 28.20% | 52.81% | 69.30% | 84.76% | 95.37% | 98.76% | 100.00% | 100.00% | 100.00% |

TABLE 2

Distribution of $\gamma'$-Phase Particles of First Specimen Counted after Automatic Stitching and Segmentation

| No | Particle size range (μm) | Particle number | Particle percentage (%) |
|---|---|---|---|
| 1 | 0.0-0.5 | 8036 | 20.02 |
| | 0.5-1.0 | 17194 | 42.86 |
| | 1.0-1.5 | 9792 | 24.41 |
| | 1.5-2.0 | 2990 | 7.45 |
| | 2.0-2.5 | 1591 | 3.96 |
| | 2.5-3.0 | 442 | 1.10 |
| | 3.0-3.5 | 61 | 0.15 |
| | 3.5-4.0 | 23 | 0.05 |
| | 4.0-4.5 | 0 | 0.00 |
| | 4.5-5.0 | 0 | 0.00 |
| | Sum | 40129 | 100.00 |

TABLE 3

Distribution of $\gamma'$-Phase Particles of Second Specimen Counted after Automatic Stitching and Segmentation

| No | Particle size range (μm) | Particle number | Particle percentage (%) |
|---|---|---|---|
| 2 | 0.0-0.5 | 6681 | 21.21 |
| | 0.5-1.0 | 15467 | 49.08 |
| | 1.0-1.5 | 6282 | 19.94 |
| | 1.5-2.0 | 1450 | 4.60 |
| | 2.0-2.5 | 781 | 2.48 |
| | 2.5-3.0 | 532 | 1.68 |
| | 3.0-3.5 | 291 | 0.92 |
| | 3.5-4.0 | 33 | 0.10 |
| | 4.0-4.5 | 0 | 0.00 |
| | 4.5-5.0 | 0 | 0.00 |
| | Sum | 31517 | 0.00 |

TABLE 4

Distribution of $\gamma'$-Phase Particles of First Specimen Obtained after Manually Modifying Images

| No | Particle size range (μm) | Particle number | Particle percentage (%) |
|---|---|---|---|
| 1 | 0.0-0.5 | 10864 | 26.37 |
| | 0.5-1.0 | 16242 | 39.44 |
| | 1.0-1.5 | 9181 | 22.29 |
| | 1.5-2.0 | 2660 | 6.46 |
| | 2.0-2.5 | 1601 | 3.89 |
| | 2.5-3.0 | 573 | 1.38 |
| | 3.0-3.5 | 51 | 0.12 |
| | 3.5-4.0 | 22 | 0.05 |
| | 4.0-4.5 | 0 | 0.00 |
| | 4.5-5.0 | 0 | 0.00 |
| | Sum | 41194 | 100 |

TABLE 5

Distribution of $\gamma'$-Phase Particles of Second Specimen Obtained after Manually Modifying Images

| No | Particle size range (μm) | Particle number | Particle percentage (%) |
|---|---|---|---|
| 1 | 0.0-0.5 | 7583 | 23.64 |
| | 0.5-1.0 | 14531 | 45.31 |
| | 1.0-1.5 | 6972 | 21.73 |
| | 1.5-2.0 | 1413 | 4.40 |
| | 2.0-2.5 | 714 | 2.21 |
| | 2.5-3.0 | 512 | 1.59 |

TABLE 5-continued

Distribution of γ'-Phase Particles of Second Specimen
Obtained after Manually Modifying Images

| No | Particle size range (μm) | Particle number | Particle percentage (%) |
|---|---|---|---|
| | 3.0-3.5 | 321 | 1.00 |
| | 3.5-4.0 | 40 | 0.12 |
| | 4.0-4.5 | 0 | 0.00 |
| | 4.5-5.0 | 0 | 0.00 |
| | Sum | 32086 | 100 |

By establishing a mathematic model, the automatic stitching of the characteristic images of the full-view-field microstructures and the automatic segmentation and identification of the precipitate particles are realized; and the quantitative distribution characterization information of the morphology, quantity, size, and position distribution and the like of plentiful near-spherical precipitate phases in a larger range is quickly obtained. The method has the features of being accurate, high-efficiency and large in statistical distribution information quantity, as well as has much more statistical representativeness compared with conventional quantitative analysis of single-view-field microstructure images.

The invention claimed is:

1. A full-view-field quantitative statistical distribution characterization method of precipitate particles in a metal material, comprising the following steps:

(1) electrolytic polishing and corrosion of a metallic material specimen:

first, performing electrolytic polishing on the metallic material specimen after mechanical polishing is performed, so that a surface of the metallic material specimen is bright, clean and smooth; and then, performing electrolytic corrosion on the metallic material specimen after electrolytic polishing is performed, so that precipitate particles stand out from the surface of the metallic material specimen;

(2) automatic collection of characteristic images of microstructures:

positioning and marking a characteristic region of the surface of the metallic material specimen on which electrolytic corrosion is performed, performing automatic collection of characteristic images of full-view-field microstructures on a marked region using a full-automatic metallographic microscope, to obtain a plurality of characteristic images of full-view-field microstructures containing the precipitate particles combined with image synthesis; and meanwhile, recording three-dimensional coordinates of the precipitate particles in different focusing positions, to obtain a plurality of 3D morphology distribution diagrams of the precipitate particles;

(3) automatic stitching and fusion of the characteristic images of full-view-field microstructures:

for the plurality of clear characteristic images of full-view-field microstructures containing the precipitate particles obtained in the step (2), acquiring mutual information for searching metallographic characteristic images through entropies and joint entropy of any two characteristic images of microstructures of different view fields using a mutual information-based image registration algorithm, and determining a position and size of adjacent overlap regions, so that automatic identification and stitching of the overlap regions of the characteristic images of full-view-field microstructures are realized; and performing mathematical processing on edge grayscales of the stitched characteristic images of full-view-field microstructures, so that the grayscales are homogenized and fused, and a characteristic image of the full-view-field microstructure in a large-range microstructure containing a plurality of the precipitate particles is obtained;

(4) automatic identification and segmentation of the precipitate particles:

performing a process of noise elimination, segmentation, binarization, hole filling, fragment removal on the characteristic image of the full-view-field microstructure in a large range containing the plurality of precipitate particles obtained in the step (3), to obtain a preprocessed image; performing Euclidean distance transformation on the preprocessed image; and performing segmentation on the preprocessed image on which Euclidean distance transformation is performed with a watershed by using a watershed algorithm, to obtain a segmented characteristic image of the full-view-field microstructure;

(5) quantitative distribution characterization of large-range full-view-field precipitate particles:

performing statistical distribution analysis of the precipitate particles on the 3D morphology distribution diagrams of the precipitate particles obtained in the step (2) and on the segmented characteristic image of the full-view-field microstructure obtained in the step (4), to obtain the position, morphology, area and equivalent circle diameter of each precipitate particle in the large-range full view field and quantitative statistical distribution data of particle number distribution and area fraction distribution within different particle size ranges, in the step (1), the metallic material specimen after mechanical polishing is performed is taken as an anode, and a stainless steel sheet is taken as a cathode;

in the process of electrolytic polishing, an electrolytic solution is a mixed solution of inorganic acid and methanol, wherein a volume ratio of inorganic acid to methanol is 1:3 to 1:4, a voltage is 20V-40V, and an electrolytic duration is 10 s-100 s; and in the process of electrolytic corrosion, an electrolytic solution is a mixed solution of inorganic acid and chromic trioxide, wherein a voltage is 0.1V-5V, an electrolytic duration is 1 s-30 s, and an electrolytic temperature is 0° C.-25° C., wherein the mixed solution of inorganic acid and chromic trioxide is prepared by adding 10 g-20 g of chromic trioxide into 150 mL-200 mL of inorganic acid solution.

2. The full-view-field quantitative statistical distribution characterization method of precipitate particles in a metal material according to claim 1, wherein: the inorganic acid in the process of electrolytic polishing is sulfuric acid; the inorganic acid in the process of electrolytic corrosion is a mixed solution of sulfuric acid and phosphoric acid, and a volume ratio of sulfuric acid to phosphoric acid is 1:15 to 1:20.

3. The full-view-field quantitative statistical distribution characterization method of precipitate particles in a metal material according to claim 1, wherein: in the step (1), the surface of the metallic material specimen on which electrolytic corrosion is performed is immersed and washed by citric acid-aqueous solution and deionized water in sequence, and the surface of the metallic material specimen is washed by absolute ethyl alcohol and is naturally dried, to guarantee the precipitate particles of the surface of the metallic material specimen against loss.

4. The full-view-field quantitative statistical distribution characterization method of precipitate particles in a metal material according to claim 1, wherein: in the step (2), the characteristic images of microstructures of all view fields are processed by means of extension of depth of field as follow: overlapping many characteristic images of microstructures in different focusing positions of a same view field in the marked region, to generate a clear characteristic image of microstructures containing precipitate particles.

5. The full-view-field quantitative statistical distribution characterization method of precipitate particles in a metal material according to claim 1, wherein: in the step (3), the process of the mutual information-based image registration algorithm is as follows:

an expression of the entropy is as follows:

$$H(X) = -\sum_{j=1}^{N} p_j \log P_j$$

where $P_j$ represents a probability distribution of the $j^{th}$ variable;

the joint entropy reflects a correlation between random variables X and Y, and the expression thereof is as follows:

$$H(X, Y) = -\sum_{x,y} P_{XY}(x, y) \log P_{XY}(x, y)$$

where $P_{XY}(x, y)$ represents the joint probability distribution of x and y; for any two characteristic images A and B of microstructures of different view fields, the mutual information thereof is expressed as:

$$MI(A,B) = H(A) + H(B) - H(A,B)$$

where H (A) represents the entropy of A, H (B) represents the entropy of B, and H (A, B) represents the joint entropy of A and B.

6. The full-view-field quantitative statistical distribution characterization method of precipitate particles in a metal material according to claim 1, wherein: in the step (4), a formula of Euclidean distance transformation is as follows:

$$\text{disf}(p(x_1,y_1), q(x_2,y_2)) = \sqrt{(x_1-x_2)^2 + (y_1-y_2)^2},$$

where p and q represent two points in the image, (x1, y1) and (x2, y2) respectively represent coordinates of p and q, and disf (p, q) represents an Euclidean distance between two points, i.e. a segment length between two points.

7. The full-view-field quantitative statistical distribution characterization method of precipitate particles in a metal material according to claim 1, wherein: the method is used to analyze precipitates in a precipitation hardening type nickel-based superalloy.

* * * * *